(12) United States Patent
Klaue

(10) Patent No.: US 9,480,508 B2
(45) Date of Patent: Nov. 1, 2016

(54) OSTEOSYNTHESIS DEVICE

(75) Inventor: Kaj Klaue, Savosa (CH)

(73) Assignee: Kaj Klaue, Savosa (CH)

( * ) Notice: Subject to any disclaimer, the term of this patent is extended or adjusted under 35 U.S.C. 154(b) by 1740 days.

(21) Appl. No.: 11/913,974

(22) PCT Filed: May 9, 2006

(86) PCT No.: PCT/CH2006/000250
§ 371 (c)(1),
(2), (4) Date: Jun. 26, 2008

(87) PCT Pub. No.: WO2006/119659
PCT Pub. Date: Nov. 16, 2006

(65) Prior Publication Data
US 2011/0082507 A1    Apr. 7, 2011

(30) Foreign Application Priority Data
May 13, 2005   (CH) .......................... 848/05

(51) Int. Cl.
*A61B 17/68*   (2006.01)
*A61B 17/72*   (2006.01)
*A61B 17/00*   (2006.01)

(52) U.S. Cl.
CPC .......... *A61B 17/7291* (2013.01); *A61B 17/68* (2013.01); *A61B 17/72* (2013.01); *A61B 2017/00004* (2013.01)

(58) Field of Classification Search
CPC .............. A61B 2017/00004; A61B 17/7291; A61B 17/701; A61B 17/7011; A61B 17/7004
USPC .................. 606/62–68, 304, 329, 74, 300; 623/21.11, 21.19
See application file for complete search history.

(56) References Cited

U.S. PATENT DOCUMENTS

| | | | | |
|---|---|---|---|---|
| 1,951,278 | A | | 3/1934 | Ericsson |
| 2,136,471 | A | * | 11/1938 | Schneider .................. 606/62 |
| 4,169,470 | A | * | 10/1979 | Ender et al. ................ 606/62 |
| 4,446,857 | A | * | 5/1984 | Otte et al. .................. 606/62 |
| 4,457,301 | A | * | 7/1984 | Walker ........................ 606/62 |
| 4,756,307 | A | * | 7/1988 | Crowninshield ............ 606/67 |
| 4,805,607 | A | | 2/1989 | Engelhardt et al. |
| 4,898,186 | A | * | 2/1990 | Ikada et al. ................. 606/62 |
| 5,053,035 | A | * | 10/1991 | McLaren .................... 606/67 |
| 5,201,734 | A | * | 4/1993 | Cozad et al. ............... 606/62 |
| 5,207,712 | A | * | 5/1993 | Cohen .................... 623/21.19 |
| 5,562,704 | A | * | 10/1996 | Tamminmaki et al. .... 606/213 |
| 5,895,396 | A | * | 4/1999 | Day et al. .................. 606/151 |
| 5,968,047 | A | * | 10/1999 | Reed .......................... 606/76 |
| 6,074,392 | A | * | 6/2000 | Durham ...................... 606/67 |

(Continued)

FOREIGN PATENT DOCUMENTS

| | | |
|---|---|---|
| DE | 3919900 | 12/1990 |
| WO | 2004/089255 | 10/2004 |

*Primary Examiner* — Jan Christopher Merene
*Assistant Examiner* — Atiya Mahmud
(74) *Attorney, Agent, or Firm* — Rankin, Hill & Clark LLP

(57) ABSTRACT

An osteosynthesis device that is used, in particular, for securing joint fragments and for the temporary splinting of toes, more particularly for treating hammer toes or other malalignments of toes. The device comprises a pin with the center axis and the length. The pin consists largely of a bioresorbable material. The pin has at least in one section of the length a non-circular cross-section that is orthogonal to the center axis and has a radius of curvature.

20 Claims, 3 Drawing Sheets

(56) References Cited

U.S. PATENT DOCUMENTS

| | | | |
|---|---|---|---|
| 6,096,060 A * | 8/2000 | Fitts et al. | 606/232 |
| 6,203,544 B1 * | 3/2001 | Gotzen | 606/308 |
| 6,352,560 B1 * | 3/2002 | Poeschmann et al. | 623/23.4 |
| 6,409,730 B1 * | 6/2002 | Green et al. | 606/232 |
| 6,551,343 B1 * | 4/2003 | Tormala et al. | 606/213 |
| 6,635,059 B2 * | 10/2003 | Randall et al. | 606/916 |
| 2002/0143335 A1 * | 10/2002 | von Hoffmann et al. | 606/67 |
| 2003/0088252 A1 * | 5/2003 | Kaikkonen et al. | 606/76 |
| 2003/0097132 A1 * | 5/2003 | Padget et al. | 606/65 |
| 2004/0030341 A1 * | 2/2004 | Aeschlimann et al. | 606/72 |
| 2004/0215194 A1 * | 10/2004 | Hehli et al. | 606/63 |
| 2006/0200150 A1 * | 9/2006 | Ilomaki et al. | 606/73 |
| 2007/0173834 A1 * | 7/2007 | Thakkar | 606/62 |

* cited by examiner

OSTEOSYNTHESIS DEVICE

PRIORITY CLAIM

This application is a National Phase application of PCT Patent Application Ser. No. PCT/CH2006/000250 filed on May 9, 2006, which claims the benefit of Switzerland Patent Application Serial No. 848/05 filed on May 15, 2005. The specifications of these applications are expressly incorporated by reference into this application in their entirety.

FIELD OF INVENTION

The invention refers to an osteosynthesis device including a pin predominantly consisting of bioresorbable material, and to a kit including an embodiment of the device and a drill bit.

BACKGROUND

Such devices can be used for various medical indications, in particular for:
A) The fixation of joint fragments, meaning fragments exhibiting both bone and cartilage elements; and
B) The temporary splinting of toes, in particular for treating hammer toes or other toe misalignments.
Joint fragments occur for instance in the following cases:
a1) in accidents, for instance in combination with ligament injuries and eventual dislocations;
a2) in chronic joint instabilities; and
a3) in growth disturbances of adolescents (so-called osteochondrosis or osteochondritis).
In the majority of these cases, the knee joint (femur), the upper ankle joint (talus) and the hip joint ((femur) are affected.

Joint fragments typically measure between 2 and 30 mm and must, for an impeccable functioning of the joint, be anatomically fixated with precision. It is in this connection essential that the joint is not immobilized for cartilage nurturing reasons. A post-operative treatment with a continuous, passive motion therapy (CPM=continuous passive motion) is recommended. Moreover, the joint must be kept stably connected to its base bone in a free moving manner.

The operations for the indications listed under A) are known as "ostechondrosyntheses". In these situations, the so-called inter-fragmentary shearing motions are particularly feared. In order to prevent these, fixations are carried out with trans-fragmentary pins inserted from the side of the joint into the epiphyseal bone. The preparation of such pins from a resorbable material is also known.

The joint fragments are mostly so small that only a single pin can be placed inside them. Several pins would also endanger the strength and blood supply of the bone portion. The joint fragments are also often positioned in such a manner as to be accessed in an orthogonal and joint-side direction only with difficulty.

The state of the art for the indications listed above under B) is the Kirschner wire-fixation of the toe joints during the healing time (soft tissue and/or bone healing), where the wire projects from the toe tip. The disadvantage of this already known Art lies in the fact that the patient is barely able to work, because he has to wear a so-called "bumper" (for instance a hard rail).

The most common operation of this kind is the arthrodesis of the proximal interphalangeal joint, meaning the growing together of the bones, where unfortunately only a joint resection (the so-called Hohmann operation) is carried out.

Also recommended is a functional operation whereby ligaments of the terminal phalanx are transferred to the base phalanx (the so-called Girdlestone and Taylor operation, 1947). Both operations require a 6-8 week mechanical immobilization.

The WO2004/089255 describes a tubular device for the temporary splinting of toes, which is implanted by a guiding wire. However, this known device possesses several disadvantages, as follows:
The round cross section of the tube causes a situation wherein individual bones can turn around the tube, meaning that a rotative securing of the implant is lacking;
An expensive operating technique (the inserted guiding wire may bend and take a wrong path; the tube may jam on the guiding wire; the tubular implant and the guiding wire are weakened in themselves (small wire size and central channeling in the tube; the application from a distal point, meaning originating from the tow body, sacrifices the distal interphalangeal joint).

SUMMARY OF INVENTION

The present invention relates to an osteosynthesis device which may include a pin with a central axis and a predetermined length. The pin predominantly consists of a bioresorbable material. The pin has, in at least one section of the length, a non-circular cross section orthogonal to the central axis. The present invention also relates to a kit. The kit may include a device which as a pin as described above and a drill which has a diameter which is smaller than, and preferably over 30% smaller than, a maximum outside diameter of the pin. Some of the advantages of the present invention are listed below.

For the indications listed under A):
A1) a rotationally stable and slide-proof fixation of the joint fragment by using a single pin; and
A2) the use of an adequate drilling material (an alternately rotating, flexible drill) and the initial drilling through a curved drill bushing;

For the indications listed under B):
B1) to guarantee a rotational stability of the implant, so as to be able to consolidate the arthrodesis in a correct and stable position and thus achieve a natural position of the toe nail and the toe body;
B2) to correct a hyperflection defect of the proximal interphalangeal joint; and
B3) to guarantee a ground contact of the toe body.

Some further advantages of the present invention are listed below:
a) the uninvolved joint (distal interphalangeal joint) can be spared;
b) the inter-fragmentary stability can be drastically improved, thus insuring consolidation; and
c) the stability is particularly preserved in rotation.

In a particular form of embodiment of the invention, the non-circular cross section of the pin is realized over only part of its total length. This allows optimizing its strength. The non-circular cross section can be made in a polygonal, preferably triangular shape. Thank to the shape of this profile, the rotational protection can be optimized.

In another form of embodiment of the invention, the central axis of the pin may be curved. The advantage of this configuration lies essentially in the fact that the anatomical axis of the toe is reconstructed in the sagittal axis.

The ground contact of the toe body is curved with a slight "bias". It has proved advantageous to intersect the tangents at both endpoints of the pin's central axis at an angle of 5°-20°. The advantage of this embodiment is in the "nailing" of the joint fragment or tubular bone which is, in case of difficult accesses done from any desired side through a penetrating bushing.

In a further form of embodiment of the invention, the pin presents on its peripheral surface at least three longitudinal edges or ridges. This achieves the advantage that the profiled edges of the pin are anchored in the cartilage or bone tissue.

The longitudinal edges or longitudinal ridges may separate from each other by concave depressions.

The maximum outside diameter of the pin is advantageously 1.5-3.5 mm, and the core diameter 1.0-2.5 mm.

In another form of embodiment of the invention, the pin tapers in the direction of the centre of the radius of curvature of the central axis. This facilitates the implantation of the pin.

The pin is preferably formed solid. The pin may be rounded off on at least one of its extremities.

The bioresorbable material forming the pin is advantageously made essentially brittle and fragile. The bioresorbable material conveniently exhibits a breaking elongation $\epsilon=(\Delta \times 100/L)<10\%$. The advantage of such a material is in its better resorbability.

In another form of embodiment of the invention, the pin is made of a reinforced, preferably self-reinforced bioresorbable material. The resorbable material may be a poly-L-lactide (PLLA) or a caprolacton. These materials offer the advantage of reabsorbing more quickly through the joint fluid. The pin advantageously consists of a copolymer of lactic acid and glycol acid, preferably in a 3:1 to 5:1 ratio. The pin may also consist of a copolymer of poly-L-lactide (PLLA) and poly (DL-lactide-co-glycolic acid) (PLGA), preferably in a 3:1 to 5:1 ratio and typically in a 4:1 ratio. The pin may also consist of a copolymer of poly-L,D-lactide.

The length of the pin conveniently runs to maximally 6 cm, preferably maximally 5 cm. The length conveniently runs to at least 3.5 cm, preferably at least 4 cm.

In another form of embodiment, the pin is adapted for the temporary splinting of toes, in particular for the treatment of hammer toes or other toe misalignments.

In a further form of embodiment, the pin is adapted for the fixation of joint fragments, in particular those with both bone and cartilage portions.

In another form of embodiment, the pin offers a particular front end designed for inserting into the bone, which is preferably formed in a blunt and preferably planar manner. The blunt configuration of the front end is particularly suitable for an application in case of an ostechondritis. A pointed configuration of the front end is on the contrary particularly suitable in case of a toe application.

In another form of embodiment, the same includes a head portion coaxially bordering the pin, which comprises an axially opposite rear end and a cross section that enlarges toward the rear end. The advantages of such a form of embodiment lie in the fact that in case of applying the device in an osteochondritis the following nailing effects are secured:
 A) thanks to the friction of the pin over an important length, an adequate stability is achieved; and
 B) in the head portion, where the friction is small because of its short length, the positive locking achieved as a result of the edge effect of the head portion provides axial stability.

In a further form of embodiment the cross-sectional area of the head portion set orthogonally to the central axis gradually enlarges in a direction toward the rear end of the head portion.

In another form of embodiment, the head portion presents a circularly cylindrical enveloping surface coaxial with the central axis, with a diameter matching the maximum outside diameter of the pin.

In another form of embodiment, the ratio between the length l of the head portion and the length L of the pin is between 1/20 and 1/3.

The invention and further developments of the invention will in the following be explained with the aid of partially simplified representation of two examples of embodiments.

DETAILED DESCRIPTION

Figure 1:
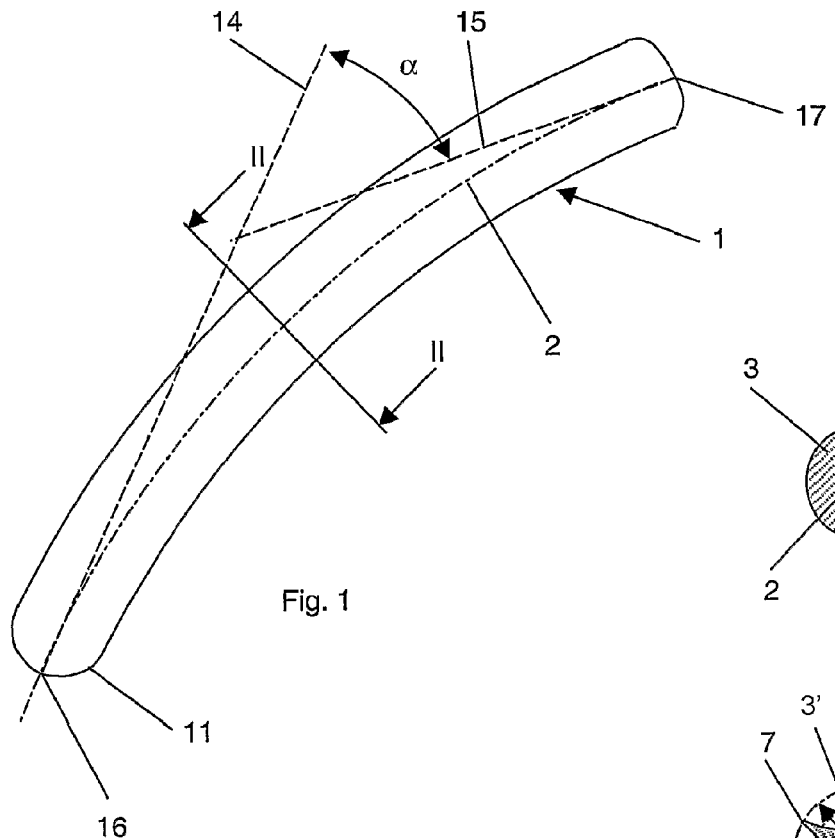
FIG. 1 is a lateral view of the pin according to the invention.
Figure 2:
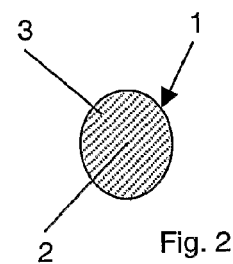
FIG. 2 is a cross section through the pin according to FIG. 1, along the line II-II.

The device for the temporary splinting of toes shown in the FIGS. 1 and 2, in particular for treating hammer toes or other toe misalignments, essentially consists of a curved pin 1 with a central axis 2 and a non-circular (in this case elliptical) cross section 3, which preferably consists of a self-reinforced poly-L,D-lactide (SR-PLA 96/4). Copolymers made of poly-L-lactide (PLLA) and poly-(DL-lactide-co-glycolic acid)(PLGA), preferably in a ratio of 4:1, are also suitable for this purpose. A mixture of 96% poly-L-lactide (PLLA) with 4% poly-D-lactide has also proved advantageous.

The pin 1 presents a curvature in the plane of the drawing, with a radius of curvature of a length of 10 cm. The tangents 14, 15 at both end points 16, 17 of the central axis 2 of the pin 1 are in this case intersecting at an angle α of 10° to 20°, typically 15°. The length of the pin 1 amounts to 3.75 cm. The surface of the pin 1 is perfectly smooth. One end of the pin 1 destined for inserting into the toe is formed in a tapering fashion, so as to terminate in a rounded tip 11.

Figure 4:
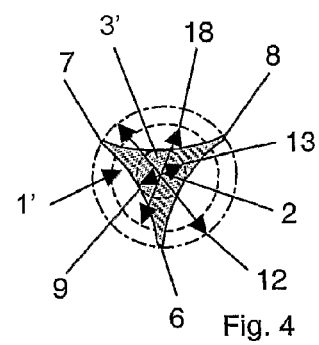
FIG. 4 is a cross section of the pin of FIG. 3 along the line IV-IV.
Figure 3:
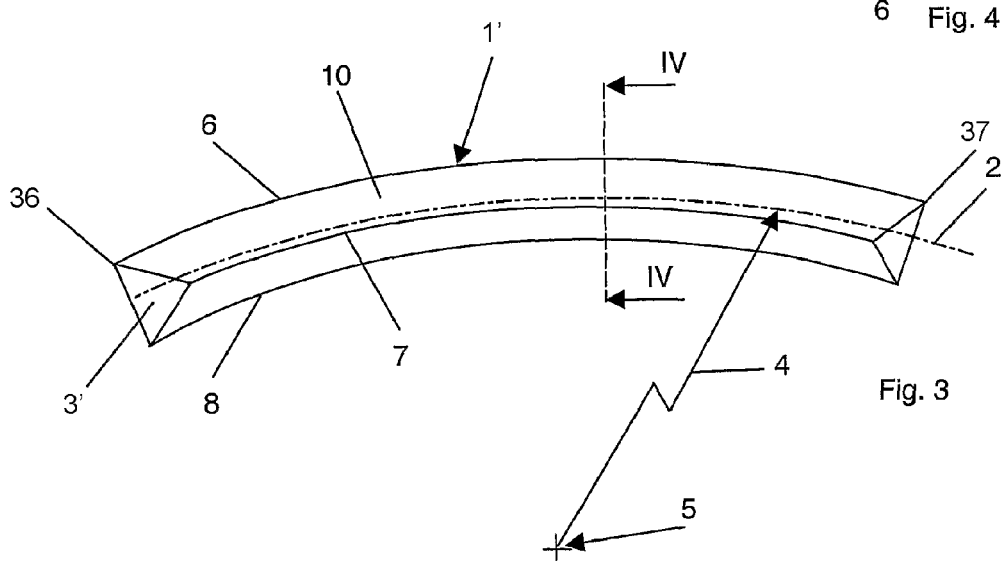
FIG. 3 is a perspective view of a modification of the pin according to FIG. 1.

The FIGS. 3 and 4 illustrate an alternative form of embodiment of the pin 1', which differs from the form of embodiment shown in FIG. 1 in the fact that the cross section 3' is noncircular. The cross section 3' is formed in a triangular rather than elliptical fashion, so that the peripheral surface 10 of the pin 1' offers three longitudinal edges or longitudinal ridges 6, 7, 8. The sides of the triangular cross section in this case have a concave conformation so that the longitudinal edges or longitudinal ridges 6, 7, 8 are separated from each other by concave depressions 9. The pin 1' presents a curvature with a radius of curvature 4 of a length of 10-15 cm, typically of 12.5 cm. The triangular cross section 3' of the pin 1' tapers in this case in the direction toward the center 5 of the radius of curvature 4. The pin 1' has a predetermined length defined between a distal-most front end 36 a proximal-most rear end 37. Furthermore, the maximum diameter 12 that can be taken through the pin 1' orthogonal to the central 2 axis remains constant over its entire predetermined length.

The borehole to be drilled into the marrow channel of the affected bones presents a bore diameter 18 which is advantageously smaller than the maximum diameter 12 of the pin 1', so as to allow the longitudinal ridges 6, 7, 8 to cut themselves into the walls of the reamed marrow channel, so that a rotational stability of the pin 1' results. The core diameter 13 of the pin 1' amounts to 1.0-2.5 mm, typically 1.6 mm.

Figure 5:
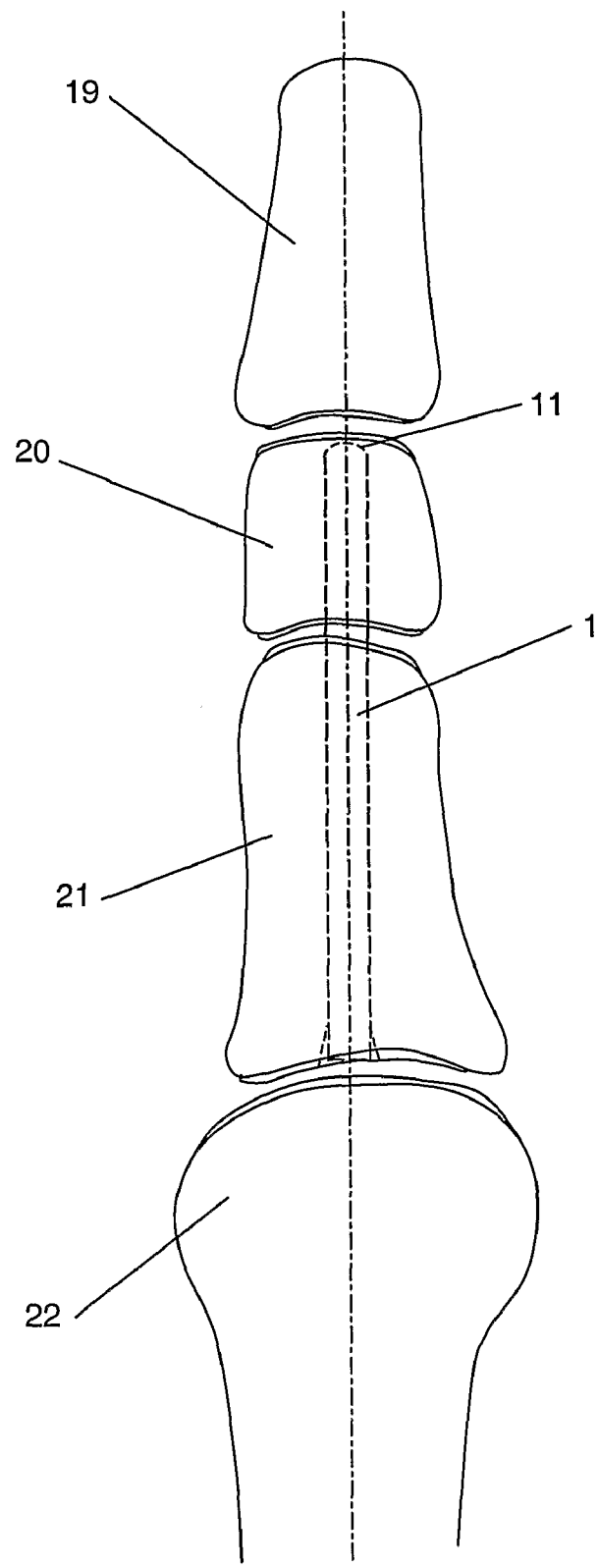
FIG. 5 is a top view onto a toe with a bioresorbable pin inserted endomedullarily.

The FIG. 5 illustrates a toe with a terminal phalanx 19, a middle phalanx 20, a base phalanx 21 and a metatarsal head 22. The insertion of the pin 1 is effected in the previously reamed marrow channels of the middle phalanx 20 and of the base phalanx 21.

Figure 8:
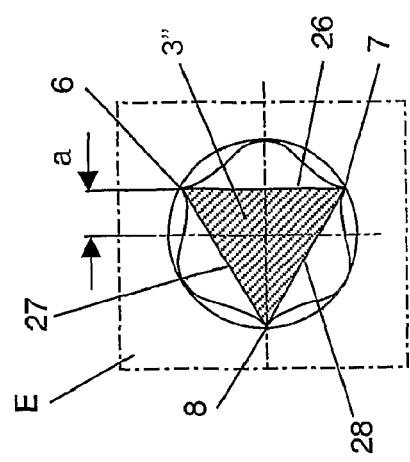
FIG. 8 is a cross section along the line II-III of FIG. 7.
Figure 6:
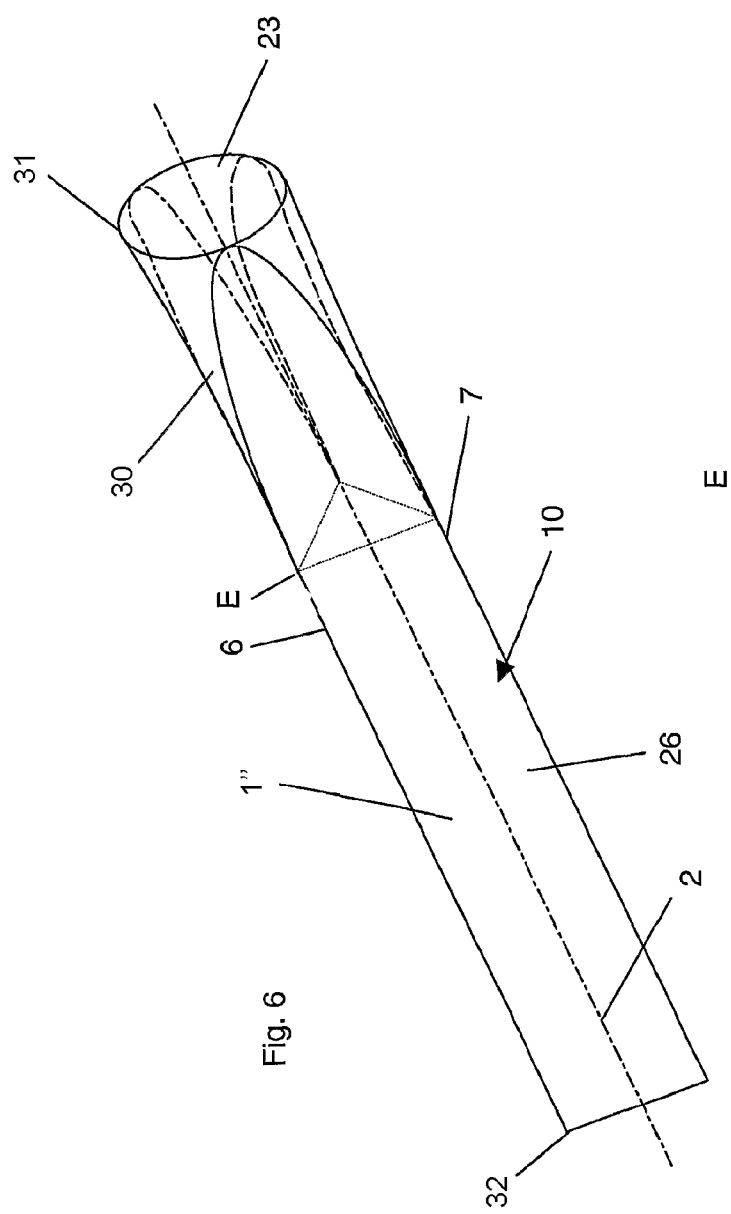
FIG. 6 is a perspective view of another form of embodiment of the pin according to the invention.
Figure 7:
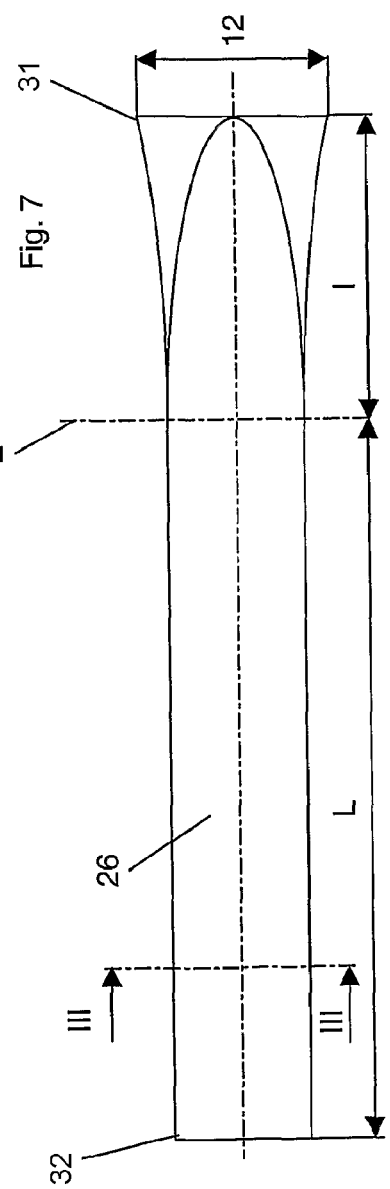
FIG. 7 is a lateral view in a direction orthogonal to a lateral surface of the form of embodiment shown in FIG. 6.

The form of embodiment represented in the FIGS. 6 to 8 comprises, apart from the pin 1", a head portion 30 coaxial with the central axis 2, where the pin 1" and the head portion 30 are formed asymmetrically to a plane E orthogonal to the central axis 2. The central axis 2, which is formed by the line connecting the points of gravity of the successive axial cross section areas extends, in the form of embodiment shown here along a straight line. The pin 1" is formed in a prismatic shape, while the head portion 30 forms a longitudinal section enlarging in a direction toward the rear end 21.

The pin 1", which is limited by the distal-most front end 32 destined for inserting into the toe and the plane E, which is taken at the where the head portion 30 begins. The pin 1" has a predetermined length L (i.e., the portion of the pin 1" extending from the distal-most front end 32 to where the head portion 30 begins at plane E), which presents over its entire length L a triangular cross section 3, so that the peripheral surface 10 of the pin shows three planar lateral surfaces 26, 27, 28 and three longitudinal edges or longitudinal ridges 6, 7, 8. The cross section 3" is limited by an equilateral triangle with a peripheral circle equal to the maximum outside diameter 12 of the pin 1, which remains constant over the entire predetermined length L.

The head portion 30 is distinguished by the fact that the plane lateral surfaces 26, 27, 28 of the pin 1" are curved in an axial direction in such a manner that the distance a between the central axis 2 and any one of the lateral surfaces 26, 27, 28 gradually increases in a direction toward the rear end 31 of the head portion 30. The head portion 30 also presents a length l and a circularly cylindrical enveloping surface with a maximum outside diameter 12 into which lateral surfaces 26, 27, 28 at the rear end 31 of the pin 1" are running into, so that the front surface 23 orthogonal to the central axis 2 at the rear end 31 of the pin 1" is a circular surface.

For a better understanding of the device according to the invention, an operating sequence in key-word style follows:
1. The patient is laid down in a supine position.
2. A dorsal access with a longitudinal cut from the middle phalanx 20 to the metatarsal head 22 follows.
3. Excision or simple longitudinal splitting of the long stretching tendon.
4. Opening up of the proximal interphalangeal joint.
5. Excision of the interphalangeal joint.
6. Bending of the distal toe.
7. Reaming of the marrow channel of the middle phalanx 20, up to the distal epiphysis.
8. Opening up of the metatarso-phalangeal joint along three-quarters of its perimeter.
9. The plantar articular plate remains.
10. Bending of the base phalanx 21.
11. Reaming of the marrow channel through the entire base phalanx 21.
12. Driving in the pin 1, from proximal to distal, through the pre-drilled hole with the borehole diameter 18 in the marrow channel, up to the distal end of the middle phalanx 20.
13. Cutting off the pin 1 at the level of the articular surface of the base phalanx 21.
14. Applying the skin suture.

Description for a Joint Fragment Fixation

On the example of an osteochondritis dissecans tali:
1. Osteotomy of the median malleolus.
2. Checking the instability of the osteochondral fragment or reduction.
3. Drilling into the fragment and the talus body and measuring the depth.
4. Driving in the pin.
5. Sawing off the pin at the cartilage level.

The profile of the fragment provides the necessary rotational stability. Inserting a second pin is not needed. In any case, there is generally no room for this purpose, and such a second pin would also endanger the vitality (blood supply).

The invention claimed is:

1. An osteosynthesis device comprising a pin having a central axis and a predetermined length defined between a proximal-most rear end and a distal-most front end,
   wherein the pin consists of a bioresorbable material selected from the group consisting of
   a copolymer of lactic acid and glycol acid,
   a copolymer of poly-L-lactide and poly(DL-lactide-co-glycolic acid),
   a copolymer of poly-L,D-lactide, and
   a caprolactone,
   wherein the pin has a non-circular cross section orthogonal to the central axis over its entire predetermined length,
   wherein the pin has a core diameter between 1.0 mm and 2.5 mm,
   wherein a maximum diameter that can be taken through the pin orthogonal to the central axis remains constant over its entire predetermined length,
   wherein the maximum diameter is between 1.5 mm and 3.5 mm,
   wherein the pin does not include an enlarged head portion,
   wherein the pin has, on its peripheral surface, one of (a) at least three longitudinal edges and (b) at least three longitudinal ridges, and
   wherein the one of (a) at least three longitudinal edges and (b) at least three longitudinal ridges are separated from each other by concave depressions.

2. The device according to claim 1, wherein the central axis is curved.

3. The device according to claim 2, wherein the pin has a radius of curvature in a range of between 10 and 15 cm.

4. The device according to claim 2, wherein tangents intersect at two endpoints of the central axis under an angle of between 5° and 20°.

5. The device according to claim 1, wherein the non-circular cross section has a polygonal shape.

6. The device according to claim 1, wherein the non-circular cross section has a triangular shape.

7. The device according to claim 1, wherein the pin tapers in a direction of a center of a curving radius of the central axis.

8. The device according to claim 1, wherein the device is adapted for a temporary splinting of toes.

9. The device according to claim 1, wherein the device is adapted for treatment of one of hammer toes and other toe misalignments.

10. The device according to claim 1, wherein the device is adapted for fixation of joint fragments.

11. The device according to claim 1, wherein the device is adapted for fixation of joint fragments with bone and cartilage elements.

12. The device according to claim 1, wherein the pin has a front end destined for inserting into bone, the front end being formed in a blunt manner.

13. The device according to claim 1, wherein the pin has a front end destined for inserting into bone, the front end being formed a planar manner.

14. The device according to claim 1, wherein an overall shape, including external dimensions and internal dimensions, of the non-circular cross section orthogonal to the central axis of the pin remain constant over its entire predetermined length.

15. A kit, comprising:
an osteosynthesis device according to claim 1; and
a drill having a diameter which is smaller than the maximum outside diameter of the pin.

16. The kit according to claim 15, wherein the diameter of the drill is over 30% smaller than the maximum outside diameter.

17. An osteosynthesis device comprising a pin having a head portion at a rear end, a central axis, and a portion having a predetermined length that extends from a distal-most front end to the head portion,
wherein the pin consists of a bioresorbable material selected from the group consisting of
a copolymer of lactic acid and glycol acid,
a copolymer of poly-L-lactide and poly(DL-lactide-co-glycolic acid),
a copolymer of poly-L,D-lactide, and
a caprolactone,
wherein the pin has a non-circular cross section orthogonal to the central axis over the entire predetermined length that does not include the head portion,
wherein the head portion has a rear end axially opposed to a front end of the pin and a cross section that widens in a direction toward the rear end of the head portion,
wherein the pin has a core diameter between 1.0 mm and 2.5 mm,
wherein a maximum diameter that can be taken through the pin orthogonal to the central axis remains constant over the entire predetermined length that does not include the head portion,
wherein the maximum diameter is between 1.5 mm and 3.5 mm,
wherein the pin has, on its peripheral surface, one of (a) at least three longitudinal edges and (b) at least three longitudinal ridges, and
wherein one of (a) the at least three longitudinal edges and (b) the at least three longitudinal ridges are separated from each other by concave depressions.

18. The device according to claim 17, wherein a surface of the cross section of the head portion orthogonal to the central axis gradually increases in a direction toward the rear end.

19. The device according to claim 17, wherein a ratio between a length of the head portion and the predetermined length of the pin is between 1/20 and 1/3.

20. A kit, comprising:
an osteosynthesis device according to claim 17; and
a drill having a diameter which is smaller than the maximum outside diameter of the pin.

* * * * *